(12) United States Patent
Lopes

(10) Patent No.: US 8,574,609 B2
(45) Date of Patent: Nov. 5, 2013

(54) DISINFECTING AND ANTIMICROBIAL COMPOSITIONS

(76) Inventor: John Alex Lopes, Troy, MI (US)

( * ) Notice: Subject to any disclaimer, the term of this patent is extended or adjusted under 35 U.S.C. 154(b) by 0 days.

(21) Appl. No.: 13/099,017

(22) Filed: May 2, 2011

(65) Prior Publication Data

US 2011/0207818 A1 Aug. 25, 2011

Related U.S. Application Data

(63) Continuation of application No. 11/337,163, filed on Jan. 20, 2006, now abandoned.

(60) Provisional application No. 60/647,464, filed on Jan. 28, 2005.

(51) Int. Cl.
*A01N 25/32* (2006.01)
*A01N 37/02* (2006.01)

(52) U.S. Cl.
USPC ..... 424/406; 424/405; 424/78.06; 424/78.07; 424/603; 424/606; 514/546; 514/547; 514/557; 514/558; 514/559; 514/560; 514/561; 514/574; 514/710; 514/738

(58) Field of Classification Search
None
See application file for complete search history.

(56) References Cited

U.S. PATENT DOCUMENTS

| 3,806,593 A | * | 4/1974 | Swanbeck et al. | 424/401 |
| 5,405,602 A | * | 4/1995 | Simmons et al. | 424/47 |
| 5,942,478 A | * | 8/1999 | Lopes | 510/130 |

\* cited by examiner

*Primary Examiner* — Neil Levy
(74) *Attorney, Agent, or Firm* — Reising Ethington PC

(57) ABSTRACT

Broad spectrum disinfecting and microbicidal compositions of biodegradable and environmentally friendly compositions containing esters formed from fatty organic alcohols and fatty carboxylic acids. These compositions display activities against the most resistant microbial forms including bacterial spores. The preparations can be used in health care, food processing, personal care and other industries where the use of harsh oxidizing chemicals is undesirable.

9 Claims, No Drawings

DISINFECTING AND ANTIMICROBIAL COMPOSITIONS

CROSS-REFERENCE TO RELATED APPLICATIONS

This application is a continuation of U.S. application Ser. No. 11/337,163 filed Jan. 20, 2006, which is a non-provisional of U.S. Provisional Patent Application Ser. No. 60/647,464 filed Jan. 28, 2005 for "Disinfecting and Antimicrobial Compositions", the entire disclosure of which is hereby incorporated by reference.

BACKGROUND OF INVENTION

1. Field of Invention

This invention relates to cleaning compositions for body, food, and food contact surfaces which reduce the risk of illness caused by harmful chemical residues, infectious agents and other disease causing and spoilage microbial agents. More particularly, the present invention provides chemical disinfecting compositions which reduce injury or inflammation to the skin. Even more particularly the present invention concerns disinfecting compositions which use safe and non-toxic chemical agents selected from alcohol esters of ethyl lactate and its homologs for preparing products with cleaning, solubilizing, antimicrobial and microbicidal properties.

2. Prior Art

Most common antimicrobial products such as chlorine, chlorine dioxide peracetic acid, ozone, hydrogen peroxide, UV- and other radiations, used to reduce microbial population on food and other contact surfaces possess highly oxidizing and sometimes destructive properties. These oxidizing chemicals and physical agents inactivate microorganisms by reacting with their organic material. However, these chemicals also react with organic food material and produce unknown chemical residues often harmful to human and animal health. Hypochlorite (chlorine) produces carcinogenic residues on food. These antimicrobial products do not have detergent action or cleaning properties. Some other cleaning preparations that are allowed on food either do not have antimicrobial and microbicidal properties or are not safe enough as the ingredients are not considered by the FDA as GRAS or food additive safe. Some other preparations have disinfecting properties without the solubilizing properties to remove harmful pesticide residues. Still some other cleaning products need to incorporate antibacterial compounds in these preparations to inhibit or kill microorganisms.

Thus, there is a need for cleaning compositions containing antimicrobial and disinfecting properties which do not exhibit the deleterious properties identified above.

The antimicrobial cleaning compositions of this invention, as described below, employ all GRAS and/or food grade additive ingredients with cleaning, solubilizing, detergent and antimicrobial properties.

SUMMARY OF INVENTION

In accordance herewith, there is provided a class of chemical compositions predicated on chemical agents that can be used to prepare antimicrobial, microbicidal and disinfecting compositions for cleaning fresh fruits, vegetables, seeds, sprouts, meats, poultry, eggs, carcasses, other food surfaces and surgical instruments as well as body parts in order to prevent, to reduce or to eliminate the risk of infection and illness arising from both chemical residues and microorganisms spread by or carried on the food, food contact and body surfaces.

The antimicrobial cleaning and disinfecting composition hereof comprises:

(a) at least one alcohol ester of an organic acid, alone, or in admixture with one or more of, (1) an antimicrobial surface active agent selected from chemicals classified as GRAS or food grade additive by the US FDA;

(2) an emulsifying surface active agents classified as GRAS or food grade additive by the US FDA;

(3) an organic acidifying agent selected from chemicals classified as GRAS or food grade additive by the US FDA which adjust the pH of the composition between 2 to 12;

(4) a chelant, either organic or inorganic, selected from chemicals classified as GRAS or food grade additive by the US FDA;

(5) a reducing agent or an antioxidant selected from chemicals classified as GRAS or food grade additive by the US FDA, and (6) a diluent to dissolve, disperse or suspend the ester and any one of the above ingredients.

The composition hereof may include other compatible ingredients, which do not reduce or interfere with the antimicrobial and cleaning properties such as for example, urea, to enhance the cleaning properties of the composition.

The composition may, additionally, include a coloring agent, fragrances, vitamins, nutritive agents and/or a thixotropic agent or other agents, which alter physical and functional properties of the composition as, desired.

The present cleaning compositions can be prepared in either concentrated liquid or powder forms as well as in gel form, or as in a foam, thus, giving operational flexibility for use. The concentrate can be further diluted to form a use composition.

For a more complete understanding of the present invention reference is made to the following detailed description and accompanying illustrative examples.

DESCRIPTION OF THE PREFERRED EMBODIMENT

As noted hereinabove, the present invention provides a cleaning and disinfecting compound using GRAS or food grade additives and which comprises an alcohol ester of an organic acid used alone or in admixture with any one of: (a) surface active agents, (b) emulsifying agents, (c) acidifying agents, (d) sequestrants or chelants, (e) reducing agents or antioxidants, and/or (f) a diluent.

Other adjuvants such as fragrances, coloring agents and the like may, also be incorporated into the composition.

With more particularity, the alcohol ester contemplated for use herein is the reaction product of a C to $C_{12}$ fatty alcohol and a $C_1$ to $C_8$ fatty acid.

The ester hereof may be represented by the formula:

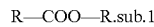

where R is an acid moiety and is either $C_nH_{2n+1}$ or $C_nH_{2n+1}O$ where n is an integer ranging from about 1 to about 8 and $R_1$ is an alcohol moiety corresponding to the formula $C_mH_{m+1}$ where m is an integer ranging from about 1 to about 12.

Respective useful esters include, for example, methyl lactate, ethyl lactate, propyl lactate, butyl lactate, etc., and the like, as well as mixtures thereof.

Among the surface active agents classified by the US FDA as generally regarded as safe (GRAS) and or classified as food additive, and having antimicrobial properties that impart additional cleaning microbicidal properties that may be incorporated into the composition hereof, include, for example lactylic esters of $C_6$ to $C_{16}$ fatty acid and the corresponding alkali salts. Other useful compounds include, for example, dioctyl sodium sulfosuccinate, sodium lauryl sulfate, salts of fatty acids and sodium mono and dimethyl naphthalene sulfonate. Mixtures of such surfactants may be used herein.

Representative of useful emulsifying agents include, for example, food grade or GRAS lecithin, polysorbate 60, polysorbate 65, polysorbate 80, sucrose fatty acid esters, salts of stearoyl 2-lactylate and the like, as well as mixtures thereof.

The acidifying agent, where used, may be selected from acetic acid, adipic acid, ascorbic acid, benzoic acid, citric acid, dehydroacetic acid, erythorbic acid, fumaric acid, glutaric acid, gluconic acid, hyaluronic acid, hydroxyacetic acid, lactic acid, malic acid, sorbic acid, succinic acid, tannic acid, tartaric acid, sulfuric acid, phosphoric acid, nitric acid, hydrochloric acid, sulfamic acid, carboxylic acid polymers, homo- or hetero-polymerized carboxylic acid such as poly lactic acid or poly lactic-glycolic acid, and the like, as well as mixtures thereof. Where used, the acidifying agent is, preferably, lactic acid.

Either an organic or inorganic sequestrating or chelating agent selected from chemicals classified as GRAS or food grade additive by the US FDA such as gluconic acid and citric acid esters such as isopropyl citrate, monoisopropyl citrate, and stearyl citrate may, also, be used herein.

Also, a reducing agent or an antioxidant selected from chemicals classified as GRAS or food additive by the US FDA such as BHT, propyl gallate, and L-cysteine, and the like, may be used herein.

The composition may be admixed with a suitable diluent be it liquid, powder, gel or foam form to dissolve or disperse or suspend the component(s). The dilutent is selected from chemicals classified as GRAS or food additive by the US FDA, and include, for example, ethyl alcohol, propylene glycol, isopropyl alcohol, water, fatty acid esters of carbohydrates including sucrose, sorbitol and the like, other useful diluents include, for example, triglycerides of fatty acids, derivatives or simple compounds of silica, cellulose, starch and natural products or synthetic polymers, and the like, as well as mixtures thereof. Preferred diluents include water, ethanol as well as propylene glycol and mixtures thereof.

Where the composition is the ester itself it is dispersed in a suitable diluent to form a concentrate containing from about 0.001% to about 99.999%, by weight, of the ester and, preferably, from about 0.01% to about 99.999%, by weight, of ester.

Where the ester is used in conjunction with any of the aforementioned additional components, generally, the ester will be present in the composition, in an amount ranging from about 0.001% to about 99.99%, by weight, based on the total weight of the concentrate.

Generally, where the additional component is a surface active agent, the concentrate will contain from about 0.01% to about 40.00%, by weight, of the surfactant based on the weight of the concentrate.

Where the ester is used with an emulsifier, the concentrate will comprise from about 0.01% to about 40.00% by weight of the emulsifier based on the weight of the concentrate.

Where the adjuvant is an acidifying agent, it will be present in an amount ranging from about 0.01% to about 40% by weight of the acidifying agent based on the weight of the acidifying concentration.

The chelant, where used, will be present in the concentrate in an amount ranging from about 0.01% to about 10% by weight, based upon the total weight of the concentrate.

With respect to the reducing agent or antioxidant, where used, in forming the concentrate it will be present in an amount ranging from about 0.01% to about 40.00% by weight, based on the weight of the concentrate.

Where the concentrate is an admixture of each of the adjuvants, the resulting composition will contain from about 0.01% to about 99.99%, by weight, of the ester; from about 0.01% to about 40.00% by weight, of the surfactant; from about 0.01% to about 40.00% by weight, of the emulsifier; from about 0.01% to about 10.00% by weight, of the chelant; from about 0.01% to about 40.00% by weight, of the reducing agent, all based upon the total weight of the concentrate.

In preparing the concentrate, it is prepared at room temperature, by admixing the components together.

In forming the use solution, the use solution will contain from about 0.01% to about 99.99% by weight, of the ester and from about 0.01% to about 99.99% by weight, of the additional component, be it any one component or a mixture thereof.

The use solution is prepared at room temperature by mixing or admixing together the concentrate with the diluent.

Where the diluent is a powder, the powder is brought into a solution or suspension with the concentrate, the powder being mixed therewithin.

Generally, the final form of the use composition will contain from about 0.01% to about 99.99%, by weight, of ester; from about 0% to about 99.99%, by weight of adjuvant or additional component and from about 0.01% to about 99.99%, by weight, based on the final form of the use composition of diluent.

The composition hereof is storage stable and exhibits antimicrobial cleaning and disinfecting properties.

For a more complete understanding of the present invention, reference is made to the following examples, which are to be constructed as illustrative not limitations of the present invention, all parts are by volume.

EXAMPLE I

This example illustrates the sporicidal activity of lactic esters against *Bacillus coagulans* spores.

One ml each of a mixture of ethyl lactate and butyl lactate (1:1) was mixed, at room temperature, with 0.1 ml of *B. coagulans* spore suspension containing $1.5 \times 10^6$ spores per ml and incubated at room temperature for five minutes. *B. coagulans* exhibit very high heat resistance and is used as an indicator for bacteria in a heat sterilization process.

After five minutes 1 ml of the test mixture was mixed with 10 mls of Butterfield's buffer, at pH 7.0. Then, 0.1 ml of the buffered test mixture was plated on a plate count in agar. The colonies were counted after 48 hrs of incubation at room temperature.

The following table, Table I, shows the results of the colony counting.

TABLE 1

Sporicidal Activity of Lactic Esters

| | |
|---|---|
| Starting Number of Spores in the inoculum: | $1.5 \times 10^6$/ml |
| Number of spores in the test (diluted 1:10): | $1.5 \times 10^5$/ml |
| Number of spores in the buffer (diluted 1:11): | $1.4 \times 10^4$/ml |
| Number of spores plated (0.1 ml): | $1.4 \times 10^3$/ml |
| Surviving number colony forming units: | 150/plate |
| Percentage killed $(1.4 \times 10^3 - 150) \times 100$: | 89.28% |

Example 1 shows that the mixture of ethyl lactate and butyl lactate displays sporicidal activity.

EXAMPLE II

This example illustrates the microbicidal activity of ethyl lactate and butyl lactate against vegetative bacteria. Example II, also, shows the minimum lethal activity (MLC) of these lactic esters against both gram positive and gram-negative bacteria.

The microbicidal activity was further investigated by determining the minimum inhibitory concentration (MIC) and minimum lethal concentrations (MLC) of these esters.

The tests were carried out in 10 ml of brain heart infusion broth. The esters were serially diluted in brain heart infusion broth of samples of, 0.1, 0.2, 0.3, 0.4 and 0.5/10 ml and challenged with 0.1 ml of 1/100 dilution of 24 hr old brain heart infusion bacterial culture. The lowest concentration determined the minimum inhibitory concentration (MIC). The samples were observed after 48 hrs at 37.degree. C. A loopful from tubes without growth were plated on BHI agar plates and observed for growth for 24 to 48 hrs at 37.degree. C. The samples with the lowest concentration of the ester without bacterial growth on the plates represented the minimum lethal concentration (MLC).

Tables 2 and 3, below, show the results of the tests.

TABLE 2

Antimicrobial Properties of Ethyl Lactate

| | | Concentration of Ethyl lactate | | | | | |
|---|---|---|---|---|---|---|---|
| Test Organism | | 0.5% | 1% | 2% | 3% | 4% | 5% |
| E. coli 0157; H7 | MLC | + | + | − | − | − | − |
|  | MLC | + | + | + | − | − | − |
| Listeria monocytogenes | MLC | + | + | + | + | + | + |
|  | MLC | + | + | + | + | + | + |
| Pseudomonas aeruginosa | MLC | + | + | − | − | − | − |
|  | MLC | + | + | + | + | − | − |
| Staphylococcus aureus | MLC | + | + | + | + | + | − |
|  | MLC | + | + | + | + | + | + |
| Salmonella typhimurium | MLC | + | + | + | + | − | − |
|  | MLC | + | + | + | + | + | + |

MIC = Minimum Inhibitory Concentration,
MLC = Minimum Lethal Concentration;
+ = growth (inactive);
− = no growth (active)

TABLE 3

Antimicrobial Properties (MLC) of Butyl Lactate

| | | Concentration of Butyl lactate | | | | | |
|---|---|---|---|---|---|---|---|
| Test Organism | | 0.5% | 1% | 2% | 3% | 4% | 5% |
| Pseudomonas aeruginosa | MLC | + | + | + | − | − | − |
| Listeria monocytogenes | MLC | + | + | − | − | − | − |

TABLE 3-continued

Antimicrobial Properties (MLC) of Butyl Lactate

| | Concentration of Butyl lactate | | | | | |
|---|---|---|---|---|---|---|
| Test Organism | 0.5% | 1% | 2% | 3% | 4% | 5% |

MIC = Minimum Inhibitory Concentration,
MLC = Minimum Lethal Concentration;
+ = growth (inactive);
− = no growth (active)

EXAMPLE III

This example illustrates the enhancement of antimicrobial activity of lactic esters by the incorporation of additional components therewith.

A series of samples of (a) methyl lactate, (b) ethyl lactate and (c) butyl lactate, alone, and in admixture with varying amounts of decyl lactate and sodium dodecyl sulfates were used to test minimum inhibitory activity (MIC) by the method described in Example II, against the cultures of E. coli 0157 H7, Listeria monocytogenes, Staphylococcus aureus, Salmonella typhi, and Pseudomonas aeruginosa. Tables 4 and 5 show that decyl lactate and sodium dodecyl sulfate enhanced inhibitory activities against the test bacteria.

TABLE 4

Enhancement of Antimicrobial Properties (MIC) of Ethyl lactate by Decyl lactylate

| Test Organism | Test Compound | 1% | 2% | 3% | 4% | 5% |
|---|---|---|---|---|---|---|
| E. coli 0157; H7 | EL | + | + | + | − | − |
|  | EL + DL | + | + | − | − | − |
| Listeria monocytogenes | EL | + | + | + | + | + |
|  | EL + DL | − | − | − | − | − |
| Staphylococcus aureus | EL | + | + | + | + | + |
|  | EL + DL | − | − | − | − | − |
| Salmonella typhi | EL | + | + | + | − | − |
|  | EL + DL | + | + | − | − | − |

MIC = Minimum Inhibitory Concentration,
+ = growth (inactive);
− = no growth (active)

In undiluted form these esters were found to kill all vegetative bacteria on contact.

TABLE 5

Enhancement of Antimicrobial Properties (MIC) of Lactic esters by Sodium dodecyl sulfate against Pseudomonas aeruginosa

| | | SDS | Concentration of Lactic Esters | | | | | |
|---|---|---|---|---|---|---|---|---|
| Test Organism | DL | ppm | 0.5% | 1% | 2% | 3% | 4% | 5% |
| Methyl lactate | MIC | 0.0 | + | + | − | − | − | − |
|  |  | 50 | − | − | − | − | − | − |
|  |  | 100 | − | − | − | − | − | − |
|  |  | 200 | − | − | − | − | − | − |
| Ethyl lactate | MIC | 0.0 | + | + | − | − | − | − |
|  |  | 50 | − | − | − | − | − | − |
|  |  | 100 | − | − | − | − | − | − |
|  |  | 200 | − | − | − | − | − | − |
| Butyl lactate | MIC | 0.0 | + | + | − | − | − | − |
|  |  | 50 | − | − | − | − | − | − |
|  |  | 100 | − | − | − | − | − | − |
|  |  | 200 | − | − | − | − | − | − |

MIC = Minimum Inhibitory Concentration,
MLC = Minimum Lethal Concentration;

TABLE 5-continued

Enhancement of Antimicrobial Properties (MIC)
of Lactic esters by Sodium dodecyl sulfate
against *Pseudomonas aeruginosa*

|  | | SDS | Concentration of Lactic Esters | | | | | |
|---|---|---|---|---|---|---|---|---|
| Test Organism | DL | ppm | 0.5% | 1% | 2% | 3% | 4% | 5% |

+ = growth (inactive);
− = no growth (active)

These results show that the microbicidal activity of lactic esters can be enhanced to include a broad spectrum activity against both bacterial spores as well as vegetative bacterial pathogens.

EXAMPLE IV

This example illustrates the MIC and MLC of esters of lactic acid against yeast: *Saccaromyces cerevisiae*.

A 0.1 ml of 1/100 dilution of 48 hr old culture of *S. cerevisiae* was used as inoculum. The test was performed using Sab. broth. The tubes were incubated at room temperature 25.degree. C. The test was read after 48 hrs. The results are shown in Tables 6 and 7 below.

TABLE 6

Antimicrobial activity against *Saccharomyces cerevisiae*

|  |  | Inhibitory (MIC)/Lethal (MLC) Concentration | | | | |
|---|---|---|---|---|---|---|
| Test Ester | Test Type | 1% | 1.5% | 2% | 3% | 4% |
| Methyl lactate | MIC | + | + | + | − | − |
|  | MLC | + | + | + | − | − |
| Ethyl lactate | MIC | + | − | − | − | − |
|  | MLC | + | + | − | − | − |
| Butyl lactate | MIC | − | − | − | − | − |
|  | MLC | − | − | − | − | − |

TABLE 7

Enhancement of Antimicrobial Properties (MIC) of Lactic esters by
Sodium dodecyl sulfate against *saccharomyces cerevisiae*

| Ester Tested | Sodium lauryl sulfate (ppm) |  | Inhibitory (MIC)/Lethal (MLC) Concentration | | | | |
|---|---|---|---|---|---|---|---|
|  |  |  | 1% | 1.5% | 2% | 3% | 4% |
| Methyl lactate | 200 | MIC | + | + | + | − | − |
|  |  | MLC | + | + | + | − | − |
| Ethyl lactate | 200 | MIC | + | − | − | − | − |
|  |  | MLC | + | + | − | − | − |
| Butyl lactate | 200 | MIC | − | − | − | − | − |
|  |  | MLC | − | − | − | − | − |

EXAMPLE V

This example shows that ethyl lactate can be used to solubilize other antimicrobial agents or ingredients that have low solubility in aqueous solutions. In this example ethyl lactate was used to prepare aqueous antifungal preparations of dehydroacetic acid.

Into a suitable reaction vessel dehydroacetic was mixed together at room temperature 5.0 parts of dehydroacetic acid in 100 ml of ethyl lactate.

A clear solution was formed. A 0.1 ml sample was added to 2 ml a wax coating sample. The mixture was homogeneous and did not show precipitate. The final concentration of dehydroacetic acid in the coating solution was 2,500 ppm. Thus, in parting antifungal properties to wax coating.

By reducing the spoilage microbial population the present esters, alone, or in combination with any of the above additives helps to increase the shelf life and/or keeping qualities of food. Thus the invention offers to prevent economic loss due to food spoilage and improves public health and curtails medical costs arising from food-borne and other infectious agents.

The alcohol esters of fatty acids hereof also display lethal activity against difficult to kill bacterial spores. These microbicidal agents can also be incorporated into household, personal care, health care and homeland security-related products. By incorporating other non-toxic, and generally regarded as safe (GRAS) or other ingredients considered as food additive by the United States Food and Drug Administration (US FDA), the technology provides the potential to replace products with toxic manifestation. In addition to microbicidal properties these agents can be used to solubilize and to remove certain water insoluble harmful residues from food.

The compositions can also be used to clean and disinfect inanimate surfaces. The composition can also used to prepare personal care and healthcare products used for preventing and reducing skin infections, either by direct application or by incorporating in ointments, bandages or other carriers. Further the chemicals can also be used to destroy harmful bacterial spores that are very resistant to known disinfecting agents.

These esters can also be formulated with other ingredients to prepare highly effective microbicidal products for cosmetic personal care, healthcare, pharmaceutical and other industries. Powerful microbicidal and cleaning products can be developed incorporating these esters in product formulations.

Having thus described the invention, what is claimed is:
1. A method of cleaning a surface comprising:
    preparing a disinfecting composition that comprises (1) at least one ester selected from the group consisting of methyl lactate, ethyl lactate, butyl lactate, propyl lactate, hexyl lactate, and octyl lactate, (2) an additive selected from the group consisting of a surface active agent, an emulsifying agent, an organic acidifying agent, a sequestrant, a chelant, a reducing agent, an antioxidant, and mixtures thereof, and (3) a diluent, and wherein the disinfecting composition is food additive safe; and
    applying the composition to a surface containing microbes, bacteria, and bacterial spores to thereby treat the surface to clean the surface and to reduce the microbial count and wherein the compound has sporicidal activity effective to kill at least 89% of the bacterial spores on the surface.
2. The method set forth in claim 1 wherein the disinfecting composition comprises an organic acidifying agent selected from the group consisting of adipic acid, ascorbic acid, azelaic acid, citric acid, dehydroacetic acid, erythorbic acid, fumaric acid, gluconic acid, hyaluronic acid, hydroxy acetic acid, lactic acid, malic acid, salicylic acid, succinic acid, tannic acid, tartaric acid, pimelic acid, suberic acid, sebacic acid, carboxylic acid polymers and mixtures thereof.
3. The method set forth in claim 2 wherein the acidifying agent comprises lactic acid.
4. The method set forth in claim 1 wherein the disinfecting composition comprises a sequestering agent selected from the group consisting of citric acid, sodium gluconate, isopro- pyl citrate, ethylenediaminetetraacetic acid, sodium acid phosphate, sodium acid pyrophosphate and mixtures thereof.

5. The method set forth in claim 1 wherein the disinfecting composition comprises a surfactant selected from the group consisting of salt and acid from of C4 to C18 alkyl, alkenyl, alkylbenzene, and naphthalene -sulfates, -sulfonates, -isethionates, -sulfoacetates, -sulfosccinates and -lactylates and mixtures thereof.

6. The method set forth in claim 5 wherein the surfactant comprises sodium lauryl sulfate, sodium dodecyl benzene sulfonate and sodium decyl lactylate or mixture thereof.

7. The method set forth in claim 1 wherein the disinfecting composition comprises an aqueous or non-aqueous diluent selected from the group consisting of water, ethyl alcohol, isopropyl alcohol, propylene glycol, glycerol, hydrogen peroxide, petroleum jelly, natural gum, silica, cellulose or mixtures thereof.

8. The method as set forth in claim 1 wherein the surface is the surface of a fruit or vegetable.

9. The method as set forth in claim 1 wherein the surface is skin.

* * * * *